US006979720B2

(12) United States Patent
Brugel et al.

(10) Patent No.: US 6,979,720 B2
(45) Date of Patent: *Dec. 27, 2005

(54) MANUFACTURE OF CERTAIN CYCLIC ESTER OLIGOMERS

(75) Inventors: Edward G. Brugel, Wilmington, DE (US); Robert Di Cosimo, Rockland, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 251 days.

This patent is subject to a terminal disclaimer.

(21) Appl. No.: 10/426,600

(22) Filed: Apr. 30, 2003

(65) Prior Publication Data

US 2004/0019177 A1   Jan. 29, 2004

Related U.S. Application Data

(60) Provisional application No. 60/380,034, filed on May 3, 2002.

(51) Int. Cl.$^7$ .......................... C08G 63/78; C08G 6/00
(52) U.S. Cl. .................. 528/274; 528/308.6; 528/491; 528/493; 528/497; 528/501; 526/67; 526/68; 526/69; 526/70; 526/206; 526/208; 524/732; 524/768; 524/770
(58) Field of Search ............................ 528/274, 308.6, 528/491, 493, 497, 501; 526/67, 68, 69, 70, 526/89, 206, 208; 524/732, 768, 770

(56) References Cited

U.S. PATENT DOCUMENTS

| | | | |
|---|---|---|---|
| 2,020,298 A | 11/1935 | Corothers et al. | |
| 5,466,744 A | 11/1995 | Evans et al. | |
| 5,661,214 A | 8/1997 | Brunelle et al. | |

OTHER PUBLICATIONS

Berkane, Christopher et al., "Lipase-Catalyzed Polyester Synthesis in Organic Medium. Study of Ring-Chain Equilibrium", Macromolecules, 1997, 30, p7729-7734.*
Mezoul, Gilles et al., "Enzyme-catalyzed syntheses of poly (1,6-hexanediyl isophthalate) and poly(1,6-hexanediyl terephthalate) in organic medium", Polymer Bulletins, 36, 541-548 (1996).*
Lavalette, Arnuad et al., "Lipase-Catalyzed Synthesis of a Pure Macrocyclic Polyester from Dimethyl Terephthalate and Diethylene Glycol", BioMacromolecules, vol. 3, No. 2, Mar./Apr. 2002.*
Biomacromolecules, Mar./Arpil 2002, Lipase-Catalyzed Synthesis of a Pure Macrocyclic Polyester form Dimethyl Terephthalate and Diethylene Glycol, Arnaud Lavalette et al.
Intramolecular Reaction in Polycondensations. I. The Theory of Linear Systems, Journal of chemical Physics, vol. 18, No. 12, Dec. 1950, Homer Jacobson et al.
Macormolecules 1997, 30-7729-7734, Lipase-Catalyzed Polyester Synthesis in Organic Medium, Study of Ring-Chain Equilibrium, Berkane et al.
2445 Polymer Bulletin 36(1966) May., No. 5, Berlin, DE., Enzyme-Catalyzed Synthesis of Poly(1,6-hexanediylisophthalate) and poly(1,6-hexanediyl terephthalate in organic medium, Gilles Mezoul.

* cited by examiner

Primary Examiner—Samuel A. Acquah

(57) ABSTRACT

Enzymes which are capable of catalyzing esterifications and/or transesterifications such as selected lipases and esterases can, under specified conditions, convert certain lower linear oligomers of polyesters to their cyclic ester oligomers in quantities greater than would be predicted by thermodynamic calculation or prior art methods. The cyclic ester oligomers are useful for the production of higher molecular weight linear polyesters.

13 Claims, No Drawings

US 6,979,720 B2

MANUFACTURE OF CERTAIN CYCLIC ESTER OLIGOMERS

CROSS REFERENCE TO RELATED APPLICATION

This application claims the benefit of the filing date of U.S. Provisional Patent Application No. 60/380,034, filed May 3, 2002.

FIELD OF THE INVENTION

Certain cyclic ester oligomers can be manufactured in relatively high yields by contacting a solution of a oligomers of an organic diacid or its diester with a diol, with one or more enzymes for (trans)esterification such as the lipases from *Candida antarctica* under certain specified conditions.

TECHNICAL BACKGROUND

Cyclic ester oligomers (CEOs) have been known for a long time, see for instance U.S. Pat. No. 2,020,298. They are known to be present in varying, usually small, quantities in many linear polyesters and have been isolated from such linear polyesters. They are often low viscosity liquids, and it has been known for a long time that they may be polymerized to higher molecular weight linear polyesters by ring opening polymerization, see for instance U.S. Pat. Nos. 5,466,744 and 5,661,214 and references cited therein. This ability to readily form a high molecular weight polymer from a relatively low viscosity liquid has made these CEOs attractive as materials for reaction injection molding type processes, wherein a low viscosity material is converted to a high molecular polymer in a mold, so that a final shaped part is obtained.

However such CEOs have been difficult and expensive to prepare, for example requiring very high dilution conditions and/or using relatively expensive starting materials such as diacyl halides in conjunction with diols and a base to react with the HCl formed, see for instance U.S. Pat. No. 5,466,744. These high manufacturing costs have in many cases prevented the use of CEOs commercially, and therefore lower cost routes to CEOs are of great interest.

More recently it has been found that polyesters can be made from carboxylic diacids or their diesters and diols using enzymes which catalyze (trans)esterification, see for instance X. Y. Wu, et al., Journal of Industrial Microbiology and Biotechnology, vol. 20, p. 328–332 (1998), E. M. Anderson, et al.; Biocatalysis and Biotransformation, vol. 16, p. 181–204 (1998); and H. G. Park, et al., Biocatalysis, vol. 11, p. 263–271 (1994). In some instances, in such reactions the production of small amounts of CEO coproducts has also been reported, see for instance G. Mezoul, et al., Polymer Bulletin, vol. 36, p. 541–548 (1996). There has also been a study reported on the amounts of CEOs which should be present in such reactions, C. Berkane, et al., Macromolecules, vol. 30, p. 7729–7734 (1997). The latter study concluded that formation of the CEOs in the enzyme catalyzed reactions followed the same type of rules that govern the formations of these CEOs in nonenzymatic catalyzed reactions, and that only small fractions of CEOs should be produced in such enzymatic reactions unless they were done under very dilute conditions. In all of these references the byproduct alcohol or water from the transesterification/esterification was removed (usually by sparging with an inert gas) to drive the polymeric product to higher molecular weight.

A recent paper, A. Lavalette, et al., Biomacro-molecules, vol. 3, p. 225–228 (2002) describes a process whereby an enzymatically catalyzed reaction of dimethyl terephthalate and diethylene glycol or bis(2-hydroxyethyl)thioether leads to essentially complete formation of the dimeric cyclic ester, while use of 1,5-pentanediol leads to a relatively high yield of the dimeric cyclic ester, along with some linear polyester. The formation of high yields of the cyclic with diethylene glycol and bis(2-hydroxyethyl)thioether to a π-stacking-type short range interaction which favored formation of the dimeric cyclic ester.

Heretofore, however, it has been unknown in the art how to produce CEOs from the reaction of aromatic dicarboxylic acids with glycols of the general formula $HOCH_2(CR^1R^2)_nCH_2OH$ (wherein $R^1$ and $R^2$ are each independently hydrogen or an alkyl group and n is 0, 1 or 2) to obtain the CEOs in an amount that is greater than that predicted by thermodynamic equilibrium, as taught by Homer Jacobson and Walter H. Stockmeyer in *Intermolecular Reaction and Polycondensation I. The Theory of Linear Systems*, The Journal of Chemical Physics, Vol. 18 Number 12, December 1950, and which is well-known to persons skilled in the art.

For instance, in the above general formula for glycols, when n=0, 1 or 2 and $R^1$ and $R^2$ are each independently hydrogen, the amount of CEOs produced that is predicted by thermodynamic equilibrium and actually is produced by the use of prior art methods is approximately 1.0, 2.5 and 0.5 weight percent CEOs, respectively, the balance being primarily linear polymer.

Surprisingly, when glycols of the above general formula are reacted with aromatic dicarboxylic acids or their esters in accordance with the method of the present invention, the amount of CEOs that can be recovered can, in some cases, be in excess of 50 weight percent.

SUMMARY OF THE INVENTION

This invention concerns a process for the production of certain cyclic ester oligomers, comprising the step of:
reacting, in a preselected solvent, components comprising:
(1) a first component which is a linear ester oligomer derived from reactants comprising an aromatic dicarboxylic acid and a diol of the general formula $HOCH_2(CR^1R^2)_nCH_2OH$, wherein $R^1$ and $R^2$ are each independently hydrogen or an alkyl group and n is 0, 1 or 2, which first component has an average degree of polymerization of about 1.5 to about 10; in the presence of
(2) a second component which is an enzyme capable of catalyzing the transesterification of esters, with the proviso that if said first component has more than 5 mole percent carboxylic acid ends, said second component is also capable of catalyzing esterification of carboxylic acids;
wherein said reacting step is carried out at a predetermined temperature at which said first component has a solubility of at least one w/v percent in said preselected solvent.

DETAILS OF THE INVENTION

Herein certain terms are used and some of them are defined below:

As used herein, the term "aromatic dicarboxylic acid" means an organic compound that includes an aromatic ring as a part of its structure, has two carboxyl groups and includes those compounds that are derived from an aromatic dicarboxylic acid or a simple derivative thereof such as a diester, or a half-acid ester of the aromatic dicarboxylic acid. The aromatic dicarboxylic acid may be substituted with one or more functional groups such as halogen, ether, thioether, and oxo (keto) which do not substantially interfere with the various reactions described in the processes herein.

By a "diol" is meant an organic compound having 2 hydroxyl groups or a simple derivative thereof. The diol may be substituted with one or more functional groups such as halogen, ether, thioether, and oxo (keto) which do not substantially interfere with the various reactions described in the processes herein.

By a "cyclic ester oligomer" is meant a cyclic compound in which is derived from an aromatic dicarboxylic acid and a diol, an aromatic hydroxycarboxylic acid, or a combination of an aromatic dicarboxylic acid, a diol and an aromatic hydroxycarboxylic acid. The various types of compounds in the CEO (diol, aromatic dicarboxylic acid, and aromatic hydroxycarboxylic acid) are connected by ester groups.

By a "dimeric" CEO herein is meant a compound made from an aromatic dicarboxylic acid and diol which has two aromatic dicarboxylic acid moieties and two diol moieties present in the CEO, while if the CEO is made from an aromatic hydroxycarboxylic acid it is derived from two such molecules. Trimeric, tetrameric, etc. CEOs have analogous definitions.

By "soluble" herein is meant that a substance has a solubility of at least about 1.0 w/v percent (based on the total of the weight of the solute and the volume of the solvent, in g and mL respectively).

By "an average degree of polymerization" (DP) is meant the number of repeat units in an oligomer chain. By a repeat unit of the polyester of a dicarboxylic acid and a diol is meant a unit having one aromatic dicarboxylic acid derived unit and one diol derived unit. A repeat unit for an aromatic hydroxycarboxylic acid is derived from a single aromatic hydroxycarboxylic acid molecule. The average degree of polymerization is determined by measuring the average molecular weight of the oligomer by gel permeation chromatography (also called size exclusion chromatography) using appropriate standards and stationary phases.

In the process a linear ester oligomer (LEO) is used. The oligomer has a DP of about 1.5 to about 10, preferably about 2.0 to about 5. The LEO is made from repeat units derived from a certain class of diols and an aromatic dicarboxylic acid. These LEOs may be readily obtained by adding a diol monomer of the specified general formula and an aromatic dicarboxylic acid monomer to the preselected solvent in the presence of the enzyme catalyst.

The diols used in the method of the invention are of the general formula $HOCH_2(CR^1R^2)_nCH_2OH$, wherein $R^1$ and $R^2$ are each independently hydrogen or an alkyl group and n is 0, 1 or 2, preferably all $R^1$ and $R^2$ are hydrogen and especially preferably n is 1 or 2.

Preferred aromatic dicarboxylic acids (or their derivatives including half-acid esters and diesters) are compounds of the formula $HO_2C(CH)_mCO_2H$ wherein m is an integer of 5 to 12, isophthalic acid, substituted isophthalic acids, terephthalic acid, substituted terephthalic acids, and 2,6-naphthalenedicarboxylic acid, and combinations thereof. More preferred aromatic carboxylic acids are terephthalic acid and isophthalic acid, and terephthalic acid is especially preferred. Any combination of preferred aromatic dicarboxylic acid and the diols specified in the general formula above may used to form a preferred CEO (or LEO).

Preferred combinations of aromatic dicarboxylic acids and diols include terephthalic acid with 1,3-propanediol and 1,4-butanediol or a mixture thereof, isophthalic acid with 1,3-propanediol, and 1,4-butanediol, or mixtures thereof.

As is known in the art, depending on how it is made the LEO may contain a variety of compounds. The LEO may be hydroxyl ended, carboxyl ended, or ester ended (by ester ended means that the end group is an ester of a monool such as methanol, for example if dimethyl terephthalate is used as one of the monomers and some ends are the original methyl esters), it may contain small amount of CEOs, and it may also contain some unreacted monomer(s), particularly if the DP is low. The presence of all or some of these types of compounds is included herein within the definition of LEO. It is preferred that the LEO be predominantly (>75 mole percent, more preferably >95 mole percent) hydroxyl and ester ended (in other words hydroxyl plus ester is >75 mole percent of the ends).

In one preferred form of the process the LEO is not made by an enzyme catalyzed process, but by another type of process. A typical nonenzymatic process to make an LEO is a thermal reaction of the diacid or a diester thereof with a diol to form the desired LEO. Such reactions are well-known in the art, see for instance H. Mark, et al., Ed., Encyclopedia of Polymer Science and Engineering, Vol. 12, John Wiley & Sons, New York, 1988, p. 28–49 and B. Elvers, et al., Ed., Ullmann's Encyclopedia of Industrial Chemistry, $5^{th}$ Ed., Vol. A21, VCH Verlagsgesellschaft mbH, Weinheim, 1992, p. 233–237, both of which are hereby included by reference. The esterification and/or transesterification reaction is carried out, usually with removal of a volatile byproduct (for example alcohol and/or water), until the desired DP is reached. Often an esterification/transesterification catalyst such as a titanate or a tin containing compound is also present. In order to make an LEO with few carboxyl end groups it is preferred that the LEO is made from a diester of an aromatic dicarboxylic acid and a diol.

Alternatively the LEO can be made by an enzyme catalyzed process. Indeed by starting with an aromatic dicarboxylic acid or a half-acid-ester or diester thereof together with the appropriate diol, LEOs can be made as intermediates in the same reactor in which the cyclization is catalyzed by the enzyme and using the same enzyme. Such reactions are known in the art, see for instance X. Y. Wu, et al., Journal of Industrial Microbiology and Biotechnology, vol. 20, p. 328–332 (1998); E. M. Anderson, et al., Biocatalysis and Biotransformation, vol. 16, p. 181–204 (1998); H. G. Park, et al., Biocatalysis, vol. 11, p. 263–271 (1994); G. Mezoul, et al., Polymer Bulletin, vol. 36, p. 541–548 (1996); C. Berkane, et al., Macromolecules, vol. 30, p. 7729–7734 (1997); and A. Lavalette, et al., Biomacro-molecules, vol. 3, p. 225–228 (2002), all of which are hereby included by reference. In some of these references where CEOs are reported to be produced the indications are that the monomers (e.g. aromatic diester and diol) first form linear aromatic polyesters, which are then converted (usually partially) to CEOs. During formation of the LEO or linear polyesters the volatile byproducts, such as an alcohol and/or water are usually removed, typically by sparging with an inert gas. The enzyme catalyzed formation of the LEO can be carried out under essentially the same conditions as the cyclization reaction which form the CEOs, except that sparging or other methods may be used to removed the volatile byproduct(s). In accordance with the present invention it is preferred that in the enzyme-catalyzed formation of the LEOs the starting materials and products are soluble in the solvent used (see definition of solubility above, and preferred solubilities, below).

The enzymes useful herein are typically those that catalyze, transesterification of esters and/or esterification of carboxylic acids, and/or hydrolysis of esters. Typical types of enzymes which may be used include lipases, proteases and esterases. For example see the chapter R. J. Kazlaukas, et al., *Biotransformation with Lipases*, in Biotechnology, $2^{nd}$ Ed, Vol. 8a, Eds. H. J. Rehm et al., Wiley-VCH, Weinheim, Germany, p. 40–191 (1998).

The enzymatic processes herein are run at temperatures at which the enzymes are active as catalysts for the desired reactions. The upper temperature limit is typically that at which the enzyme ceases to be an active catalyst. Oftentimes this is the temperature at which the enzyme is denatured in the reaction medium. This upper temperature will vary with the enzyme used and the process ingredients, especially the preselected solvent, used. Typically these temperatures may range from about 0° C. to about 130° C. (the latter using specialty enzymes for higher temperatures, such as enzymes isolated from thermophillic microorganisms). Higher temperatures (but below the temperature at which the enzyme ceases to be active) are usually preferred because reaction(s) are often faster and solubilities of the various process ingredients are usually higher at higher temperatures.

As noted above, "soluble" herein means that a substance has a solubility in the preselected solvent at the predetermined reaction temperature of at least 1.0 w/v percent in the solvent. Preferably the solubility is at least about 3 w/v percent, more preferably at least about 5 w/v percent. It is especially preferred that all of the process ingredients (except for the enzyme catalyst) are totally soluble in the preselected solvent at the predetermined reaction temperature throughout the enzyme catalyzed process. However, at the end of the process for example, after separation of the enzyme catalyst, the temperature of the process liquid may be lowered to precipitate the CEOs to facilitate their isolation (as by filtration).

In order to meet the criteria above for solubility, the preselected solvent needs to be carefully chosen. Typically the ingredient with the poorest solubility is the LEO, or sometimes in the case of diols with few carbon atoms such as ethylene glycol, the diol. These compounds are typically soluble in somewhat polar solvents. However it is also preferred that the solvent not contain an active hydrogen group such as hydroxyl, carboxyl, primary or secondary amino, etc. Thus polar solvents such as o-dichlorobenzene, phenyl ether, chlorobenzene, methyl t-butyl ether, diisopropyl ether, tetrahydrofuran, acetone, acetonitrile, 1,4-dioxane, N,N-dimethylformamide, dimethyl sulfoxide, 1,1,1-trichloroethane and dichloromethane are favored. Some relatively non-polar preselected solvents, including hydrocarbons such as toluene, xylene, cyclohexane, heptane, iso-octane, and halocarbons such as perchloroethylene, may also be used in the method of the present invention so long as the solubility of the LEO in the preselected at the predetermined reaction temperature is at least one w/v percent.

Concentrations of the LEOs in the process are typically at least 1 to about 25 w/v percent, more typically about 3–15 w/v percent, based on the total weight of the solute and the volume of the solvent in g and mL, respectively. The upper limit for these concentrations may be dictated in part by the desire to retain the LEOs in solution. The concentration (w/v percent) of the enzyme, either unimmobilized or immobilized, preferably ranges from about 0.01 g/mL to about 250 mg/mL, more preferably about 0.50 mg/mL to about 50 mg/mL. The specific activity of the unimmobilized enzyme preferably range from about 0.1 IU/mg of protein to about 30,000 IU/mg of protein, where an IU is an International Unit of enzyme activity and corresponds to the conversion of 1 micromole of substance per minute; for esterification or transesterification enzyme specific activity is often measured against a standard substrate, such as tributyrin. The enzyme need not be soluble in the reaction mixture, and may be attached to a solid material (supported), see for instance G. E. Bickerstaff, Ed., Immobilization of Enzymes and Cells, Humana Press, Totowa, N.J., 1997. Supports may include materials such as diatomaceous earth, polysaccharides (for example chitosan, alginate or carrageenan), titania, silica, alumina, polyacrylates and polymethacrylates, and ion exchange resins, and the enzyme may be adsorbed, covalently attached, or ionically attached, or in the form of crosslinked enzyme crystals (CLECS). The specific activity of the immobilized enzyme is preferably about 0.1 IU/g immobilized enzyme to about 2000 IU/g immobilized enzyme, more preferably about 10 IU/g immobilized enzyme to about 500 IU/g of immobilized enzyme. The enzyme make be recycled and reused in the process (for example by filtering off the enzyme from the process solution), assuming it has retained activity for catalyzing the desired reaction(s).

The process may be run as a batch, semibatch or continuous process. If volatile byproducts are removed using a flow of an inert gas (for example sparging), the volatiles in the gas may be recovered, for example by cooling the gas and condensing the volatiles, and/or the gas may be recycled in the process.

The desired CEO(s) may be recovered by normal techniques. For example if the CEO is a solid it may be recovered from solution by cooling the solution and/or removing some or all of the solvent, and recovering the solid CEO, for example by filtration. If there is some linear polyester (of any molecular weight) remaining in the process it may be possible to separate the CEO(s) from the linear polyester by differential precipitation from one or more solvents.

Preferably in the present process at least about 10 mole percent [based on the type of ingredient (e.g. diol, aromatic diester, etc.) present in the smallest stoichiometric amount], more preferably at least about 25 mole percent, especially preferably at least about 50 mole percent, very preferably at least about 75 mole percent, and highly preferably at least about 90 mole percent of the LEOs are converted in the process to one or more CEOs.

Preferred CEOs from the present process are predominantly (>50 mole percent, more preferably >75 mole percent) dimers, trimer and tetramers, more preferably dimers and trimers. In any of the of the CEO products obtained in this process some higher CEOs may also be present.

If the CEOs which are products of the present process are polymerized, they are useful for the same purposes as their linear polyester polymers. For example poly(ethylene terephthalate) is useful for fiber, films and for moldings such as electrical and automotive parts, while poly(butylene terephthalate) is useful for molding for electrical and automotive parts.

In the Examples, the following abbreviations are used:
DMT—dimethyl terephthalate
LCMS—liquid chromatography/mass spectrometry
ODCB—o-dichlorobenzene
BDO—1,4-butanediol
PDO—1,3-propanediol
RT—room temperature
T—terephthalic acid In Examples 1–4 samples were analyzed by LCMS using the following technique. Approximately 10 drops of the reaction mixture were placed in 1.5 ml of o-cresol. The o-cresol mixture was heated at 100 to 125° C. for 5 min, with stirring. Then, 5 drops of the o-cresol solution were added to 3 ml of chloroform and the mixture shaken and filtered through a 0.45 micron filter (Acrodisc® CR 25 mm syringe filter, Gelman Laboratory) into a liquid chromatograph sample vial. Analysis was carried out using a Hewlett-Packard® 1100 Liquid Chromatograph equipped with a HP G1315A UV Diode array detector and a HP G1946A Mass Spectrometer detector. Two PLGel® 50 Angstrom columns were utilized with $CHCl_3$ as the eluant at a rate of 1 ml/min. Cyclic oligomer peaks were identified via mass chromatographic spectrum and, where available, samples of pure cyclic oligomer extracted from the corresponding high molecular weight polymer. Concentrations of cyclic oligomers were determined via uncorrected area percent calculations.

EXAMPLE 1

Reaction of DMT and BDO in Toluene in the Presence of a Lipase

A 250 ml 3-neck flask was fitted with a Claisen head and condenser, a thermocouple, a nitrogen purge tube, magnetic stirring bar and heating mantle. The flask was charged with 100 ml toluene (dried over 4A activated molecular sieves), 4.85 g DMT (0.025 mole, Aldrich Chemicals), and 2.25 g BDO (0.025 mole, Aldrich Chemicals). The reaction mixture was heated, with stirring, to 60° C., until all of the DMT was in solution. One g of CHIRAZYME L-2, c-f C2, lyo (ID #2207257 Biocatalytics, 39 Congress St, Pasadena Calif.) was added to the reaction mixture and the temperature increased over 2 h to 80° C. The nitrogen purge was set at 300 ml/min and the tip of the inlet tube was placed approximately 1" below the surface of the reaction mixture. The reaction mixture was maintained at 80° C. for 24 h. During this time an additional 50 ml of toluene were added to replaced toluene purged from the reaction flask. LCMS sampling indicated that during this time period the majority of the DMT had been converted to low molecular weight oligomers. The temperature and nitrogen purge were maintained for an additional 48 h. During this time period an additional 100 ml of fresh toluene were added. At the end of this time period the reaction mixture was milky white, indicating the presence of a precipitate. The reaction mixture was cooled to RT, during which time the amount of precipitate increased. The mixture was filtered and the precipitate dissolved in chloroform and filtered in order to separate the soluble product from the CHIRAZYME L-2 Lipase. The toluene filtrate and the chloroform solution were combined and the solvents removed using a rotary evaporator. The remaining solid, 1.2 grams, was analyzed by LCMS and found to contain 50% by weight of the BDO/T cyclic dimer and trimer, formula weights 440 and 660 amu, respectively.

EXAMPLE 2

Reaction of DMT and BDO in ODCB in the Presence of a Lipase

A 1000 ml reaction kettle was fitted with a Soxhlet extractor containing 4A molecular sieves, a thermocouple, a nitrogen purge tube, a magnetic stirring bar and a heating mantle. The flask was charged with 500 ml ODCB, 4.85 g DMT (0.025 mole, Aldrich Chemicals), and 2.25 g BDO (0.025 mole, Aldrich Chemicals). The reaction mixture was heated, with stirring, to 60° C., until all of the DMT was in solution. Two g of CHIRAZYME L-2, c-f C2, lyo (ID #2207257 Biocatalytics, 39 Congress St, Pasadena Calif.) was added to the reaction mixture and the temperature increased over 2 h to 80° C. The nitrogen purge was set at 300 ml/min and the tip of the inlet tube was placed approximately 2.5 cm below the surface of the reaction mixture. The reaction mixture was maintained at 80° C. for 24 h. During this time 100 mg of demineralized water was added. LCMS sampling indicated that during this period the majority of the DMT had been converted to low molecular weight linear oligomers. The temperature and nitrogen purge were maintained for an additional 48 h. During this period an additional 100–500 mg of demineralized water were added. At the end of this period the reaction mixture was milky white, indicating the presence of a precipitate. The reaction mixture was cooled to RT, during which time the amount of precipitate increased. The mixture was filtered and the precipitate dissolved in chloroform and filtered in order to separate the soluble product from the CHIRAZYME L-2 Lipase. The ODCB filtrate and the chloroform were combined and the concentration of cyclic oligomers determined by LCMS. The LCMS analysis identified the presence of the BDO/T cyclic dimer (7.32% by weight) and trimer (7.0% by weight), formula weights 440 and 660 amu, respectively. A total yield of 14.32% cyclic oligomer was obtained.

EXAMPLE 3

Reaction of DMT and BDO in ODCB in the Presence of a Lipase

A 1000 ml reaction kettle was fitted with a Soxhlet extractor containing 4A Molecular Sieves, a thermocouple, a nitrogen purge tube, a magnetic stirring bar and a heating mantle. The flask was charged with 500 ml ODCB, 2.40 g DMT (0.0125 mole, Aldrich Chemicals), and 1.10 g BDO (0.0125 mole, Aldrich Chemicals). The reaction mixture was heated, with stirring, to 60° C., until all of the DMT was in solution. Two g of CHIRAZYME L-2, c-f C2, lyo (ID #2207257 Biocatalytics, 39 Congress St, Pasadena Calif.) was added to the reaction mixture and the temperature increased over 2 h to 80° C. The nitrogen purge was set at 300 ml/min and the tip of the inlet tube was placed approximately 2.5 cm below the surface of the reaction mixture. The reaction mixture was maintained at 80° C. for 24 h. During this time 100 mg of demineralized water was added. LCMS sampling indicated that during this time the majority of the DMT had been converted to low molecular weight linear oligomers. The temperature and nitrogen purge were maintained for an additional 48 h. During this time an additional 100–500 mg of demineralized water were added. At the end of this time the reaction mixture was milky white, indicating the presence of a precipitate. The reaction mixture was cooled to RT, during which time the amount of precipitate increased. The mixture was filtered and the precipitate dissolved in chloroform and filtered in order to separate the soluble product from the CHIRAZYME L-2 Lipase. The ODCB filtrate and the chloroform were combined and the concentration of cyclic oligomers determined by LCMS. The LCMS analysis identified the presence of the BDO/T cyclic dimer (10.6% by weight), trimer (36.5% by weight) and tetramer (11.2% by weight), formula weights 440, 660 and 880 amu, respectively. A total yield of 58.3% cyclic oligomer was obtained.

EXAMPLE 4

Reaction of DMT and PDO in ODCB in the Presence of a Lipase

A 1000 ml reaction kettle was fitted with a Soxhlet extractor containing 4A molecular sieves, a thermocouple, a nitrogen purge tube, a magnetic stirring bar and a heating mantle. The flask was charged with 750 ml ODCB, 24.25 g DMT (0.125 mole, Aldrich Chemicals), and 9.50 g PDO (0.125 mole, Aldrich Chemicals). The reaction mixture was heated, with stirring, to 60° C., until all of the DMT was in solution. Two g of CHIRAZYME L-2, c-f C2, lyo (ID #2207257 Biocatalytics, 39 Congress St, Pasadena Calif.) was added to the reaction mixture and the temperature increased over 2 h to 80° C. The nitrogen purge was set at 300 ml/min and the tip of the inlet tube was placed approximately 2.5 cm below the surface of the reaction mixture. The reaction mixture was maintained at 80° C. for 24 h. During this time 100 mg of demineralized water was added. LCMS sampling indicated that during this time period the majority of the DMT had been converted to low molecular weight linear oligomers. The temperature and nitrogen purge were maintained for an additional 48 h. During this time period an additional 100–500 mg of demineralized water were added. At the end of this period the reaction mixture was milky white, indicating the presence of a precipitate. The reaction mixture was cooled to RT, during which time the amount of precipitate increased. The mixture was filtered and the precipitate dissolved in chloroform and filtered in order to separate the soluble product from the CHIRAZYME L-2 Lipase. The ODCB filtrate and the chloroform were combined and the concentration of cyclic oligomers determined by LCMS. The LCMS analysis identified the presence of the PDO/T cyclic dimer (9.4% by weight) and trimer (3.2% by weight), formula weights 412, and 618 amu, respectively. A total yield of 12.2% cyclic oligomer was obtained.

What is claimed is:

1. A process for the production of certain cyclic ester oligomers, comprising the step of:
    reacting, in a preselected solvent, components comprising:
    (1) a first component which is a linear ester oligomer derived from reactants comprising an aromatic dicarboxylic acid and a diol of the general formula $HOCH_2(CR^1R^2)_nCH_2OH$, wherein $R_1$ and $R_2$ are each independently hydrogen or an alkyl group and n is 0, 1 or 2, which first component has an average degree of polymerization of about 1.5 to about 10; in the presence of
    (2) a second component which is an enzyme capable of catalyzing transesterification of esters, with the proviso that if said first component has more than 5 mole percent carboxylic acid ends, said second component is also capable of catalyzing esterification of carboxylic acids;
    wherein said reacting step is carried out at a predetermined temperature at which said first component has a solubility of at least one w/v percent in said preselected solvent.

2. A process in accordance with claim 1 wherein said first component has a solubility of at least three w/v percent in said preselected solvent.

3. A process in accordance with claim 1 wherein said first component has a solubility of at least five w/v percent in said preselected solvent.

4. A process in accordance with claim 1 wherein n is 1 or 2.

5. A process in accordance with claim 1 wherein said first component has an average degree of polymerization of about 2.0 to 5.0.

6. A process in accordance with claim 1 wherein said first component the linear ester oligomer, is derived from an aromatic dicarboxylic acid selected from the group consisting of diesters, half-acid esters, compounds of the formula $HO_2C(CH)_mCO_2H$ wherein m is an integer of 5 to 12, isophthalic acid, substituted isophthalic acids, terephthalic acid, substituted terephthalic acids, and 2,6-naphthalenedicarboxylic acid, and combinations thereof.

7. A process in accordance with claim 1 wherein said second component, said enzyme, is selected from the group consisting of lipases, proteases and esterases.

8. A process in accordance with claim 1 wherein said second component, said enzyme, is unsupported.

9. A process in accordance with claim 1 wherein said second component, said enzyme, is supported.

10. A process in accordance with claim 10 wherein said second component, said enzyme, is supported by materials selected from the group consisting of diatomaceous earth, polysaccharides including chitosan, alginate or carrageenan, titania, silica, alumina, polyacrylates and polymethacrylates.

11. A process in accordance with claim 1 wherein said preselected solvent is selected from the group consisting of o-dichlorobenzene, phenyl ether, chlorobenzene, methyl t-butyl ether, di-isopropyl ether, tetrahydrofuran, acetone, acetonitrile, 1,4-dioxane, N,N-dimethylformamide, dimethyl sulfoxide, 1,1,1-trichloroethane, dichloromethane, toluene, xylene, cyclohexane, heptane, iso-octane and halocarbons such as perchloroethylene.

12. A process in accordance with claim 1 wherein said predetermined reaction temperature ranges from 0° C. to 130° C.

13. A process in accordance with claim 1 wherein said predetermined reaction temperature is about 80° C.

* * * * *